United States Patent
Jones

(10) Patent No.: US 11,821,775 B2
(45) Date of Patent: Nov. 21, 2023

(54) MASS FLOW METER

(71) Applicant: The Johns Hopkins University, Baltimore, MD (US)

(72) Inventor: Jonathan P. Jones, Hanover, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/691,231

(22) Filed: Mar. 10, 2022

(65) Prior Publication Data

US 2022/0357191 A1 Nov. 10, 2022

Related U.S. Application Data

(60) Provisional application No. 63/186,358, filed on May 10, 2021.

(51) Int. Cl.
*G01F 1/80* (2006.01)
*G01F 1/684* (2006.01)
(Continued)

(52) U.S. Cl.
CPC .................. *G01F 1/80* (2013.01); *G01F 1/34* (2013.01); *G01F 1/684* (2013.01); *G01F 1/86* (2013.01);
(Continued)

(58) Field of Classification Search
CPC ... G01F 1/80; G01F 1/34; G01F 1/684; G01F 1/86; G01F 1/88; A61M 2205/3334
See application file for complete search history.

(56) References Cited

U.S. PATENT DOCUMENTS 5,827,977 A * 10/1998 Ortiz ..................... G01F 1/363
73/861.72
7,870,794 B2  1/2011 Bickmann et al.
(Continued)

FOREIGN PATENT DOCUMENTS

CA 2187029 A1 * 8/1996
CA 2819818 A1 * 1/2014 ............. E21B 47/10
(Continued)

OTHER PUBLICATIONS

Baker, Roger C., "Flow Measurement Handbook—Industrial Designs, Operating Principles, Performance, and Applications," 2nd Ed., Cambridge University Press, Aug. 2016, available online at https://www.cambridge.org/core/books/flow-measurement-handbook/2DA390E440E1F925263337563501E649 (last accessed Dec. 12, 2022), chapter 8, pp. 195-233.
(Continued)

*Primary Examiner* — Ryan D Walsh
(74) *Attorney, Agent, or Firm* — Noah J. Hayward

(57) ABSTRACT

A mass flow meter includes an arcuate tube section that is semi-circular, an inner pressure sensor disposed on an inner curvature portion of the arcuate tube section and configured to capture an inner pressure measurement of the flowing fluid, an outer pressure sensor disposed on an outer curvature portion of the arcuate tube section and configured to capture an outer pressure measurement of the flowing fluid, and processing circuitry. The processing circuitry may be configured to receive the inner pressure measurement and the outer pressure measurement, determine a pressure difference between the inner pressure measurement and the outer pressure measurement, and determine a mass flow rate of the flowing fluid passing through the arcuate tube section based on the pressure difference and a fluid density of the flowing fluid.

20 Claims, 6 Drawing Sheets

(51) Int. Cl.
*G01F 1/34* (2006.01)
*G01F 1/86* (2006.01)
*G01F 1/88* (2006.01)

(52) U.S. Cl.
CPC ....... *G01F 1/88* (2013.01); *A61M 2205/3334* (2013.01)

(56) References Cited

U.S. PATENT DOCUMENTS

| | | | | |
|---|---|---|---|---|
| 2008/0264182 | A1* | 10/2008 | Jones | G01F 1/363 73/861.63 |
| 2010/0056732 | A1* | 3/2010 | McElvain | B01J 19/0006 73/861.47 |
| 2012/0055263 | A1* | 3/2012 | Konzelmann | G01F 1/34 73/861.18 |
| 2016/0303527 | A1* | 10/2016 | Hodges | G01F 1/40 |
| 2022/0090948 | A1* | 3/2022 | Swartz | G06F 30/20 |

FOREIGN PATENT DOCUMENTS

| | | | | |
|---|---|---|---|---|
| CN | 103090917 | A * | 5/2013 | ............ G01F 1/206 |
| CN | 204286513 | U * | 4/2015 | ............... G01F 1/34 |
| CN | 111928910 | A * | 11/2020 | |
| EP | 2851099 | A1 * | 3/2015 | .......... A61M 1/1086 |
| FR | 2565344 | A1 * | 12/1985 | |
| FR | 2649790 | A1 * | 1/1991 | |
| GB | 2430269 | A * | 3/2007 | ............... G01F 1/44 |
| JP | 2021117033 | A * | 8/2021 | ............ G01F 1/363 |
| WO | WO-9936748 | A1 * | 7/1999 | ............... G01F 1/34 |
| WO | WO-2008033035 | A1 * | 3/2008 | ............... G01F 1/34 |

OTHER PUBLICATIONS

Meng, X-J. et al., "The CFD simulation and experimental research of the V type elbow flowmeter," 15th Flow Measurement Conference (FLOMEKO), Oct. 13-15, 2010, Taipei, Taiwan, Paper B9-5, available online at https://www.proceedings.com/11053.html and https://www.imeko.org/publications/tc9-2010/IMEKO-TC9-2010-085.pdf (last accessed Dec. 12, 2022), pp. 1-7.

* cited by examiner

MASS FLOW METER

CROSS-REFERENCE TO RELATED APPLICATIONS

This application claims priority to and the benefit of prior-filed, U.S. Provisional Application No. 63/186,358 filed on May 10, 2021, the entire contents of which are hereby incorporated herein by reference.

STATEMENT OF GOVERNMENTAL INTEREST

This invention was made with Government support under contract number N00024-13-D-6400 awarded by the Naval Sea Systems Command (NAVSEA). The Government has certain rights in the invention.

TECHNICAL FIELD

Example embodiments generally relate to fluid measurement technologies, and in particular fluid flow measurement devices including devices that can measure mass flow.

BACKGROUND

Meters that measure the mass flow rate of a fluid passing through a tube are often referred to as mass flow meters or inertial flow meters. Such meters measure the mass per unit time, for example, in kilograms per second, of a fluid passing through a device. The mass flow rate is related to volumetric flow rate (e.g., cubic meters per second) and the fluid density. In this regard, the mass flow rate is the volumetric flow rate multiplied by the fluid density. Based on this relationship, it can be seen that when the fluid density is constant the mass flow rate can be fairly readily determined if the volumetric flow rate can be determined. Determining the volumetric flow rate can be complex and when the fluid density varies with a system, the mass flow rate can be even more difficult to determine. Varying fluid densities within a system are rather common because fluid density can be affected by a variety of factors including temperature, pressure, and composition, as well as other factors.

A common example of a mass flow meter is a Coriolis flow meter. The Coriolis flow meter includes two bent flow tubes that twist relative to each other when a fluid passes through the tubes. The twisting is due to forces exerted by the fluid flow on the tubes. Often, the tubes are vibrated at a resonant frequency of the tubes. When no flow is passing through the tubes, the vibration movement of the tubes is in-phase. However, when a fluid passes through the tubes, the tubes move differently due to the induced twisting, such that the vibratory movement of the tubes become out-of-phase. The phase difference between the tube movement is directly proportional to the mass flow rate, and the change in frequency is proportional to the fluid density. As such, the mass flow rate can be determined using a Coriolis flow meter.

While Coriolis flow meters are quite useful for measuring mass flow rates, such meters also have drawbacks. The construction of Coriolis flow meters is quite complex and requires that the tubes are carefully constructed and controlled. The mechanical twisting of the tubes must be measured using carefully calibrated sensors that are able sense such physical movements. Finally, Coriolis flow meters are often unable to measure, for example, low gas flows at low pressures. This is because such low gas flow may not generate sufficient inertia to cause the tubes of the meter to detectably twist, thereby undermining the principles relied upon to make the necessary measurements. Accordingly, while Coriolis flow meters are useful for measuring mass flow rates in some instances, such meters are difficult to construct and maintain, and can be limited in application. As such, there is a need for further innovation and improvements in the area of mass flow rate measurement.

BRIEF SUMMARY

According to some non-limiting example embodiments, a mass flow meter is provided. The mass flow meter may include an arcuate tube section having an arc tube input for receiving a flowing fluid into the arcuate tube section and an arc tube output for outputting the flowing fluid out of the actuate tube section. In this regard, the arcuate tube section may include a semi-circular tube section. The mass flow meter may further include an inner pressure sensor disposed on an inner curvature portion of the arcuate tube section and configured to capture an inner pressure measurement of the flowing fluid, an outer pressure sensor disposed on an outer curvature portion of the arcuate tube section and configured to capture an outer pressure measurement of the flowing fluid, and processing circuitry. The processing circuitry may be configured to receive the inner pressure measurement from the inner pressure sensor, receive the outer pressure measurement from the outer pressure sensor, determine a pressure difference between the inner pressure measurement and the outer pressure measurement, and determine a mass flow rate of the flowing fluid passing through the arcuate tube section based on the pressure difference and a fluid density of the flowing fluid.

According to other non-limiting, example embodiments, another mass flow meter is provided. The mass flow meter may include an arcuate tube section having an arc tube input for receiving a flowing fluid into the arcuate tube section and an arc tube output for outputting the flowing fluid out of the arcuate tube section. In this regard, the arcuate tube section may be semi-circular. The mass flow meter may further include an inner pressure sensor disposed at an inner apex of the arcuate tube section and configured to capture an inner pressure measurement of the flowing fluid at the inner apex and an outer pressure sensor disposed at an outer apex of the arcuate tube section and configured to capture an outer pressure measurement of the flowing fluid at the outer apex. The mass flow meter may further include an absolute pressure sensor configured to capture an absolute pressure measurement within tubing of the mass flow meter, a temperature sensor configured to capture a temperature measurement of the flowing fluid within the tubing of the mass flow meter, and processing circuitry. The processing circuitry may be configured to receive the inner pressure measurement, the outer pressure measurement, the absolute pressure measurement, and the temperature measurement. Additionally, the processing circuitry may be configured to determine a pressure difference between the inner pressure measurement and the outer pressure measurement, determine a fluid density of the flowing fluid based on the absolute pressure measurement and the temperature measurement, and determine a mass flow rate of the flowing fluid passing through the arcuate tube section based on the pressure difference and the fluid density.

According to other non-limiting, example embodiments, a method for determining, by a mass flow meter, a mass flow rate of a flowing fluid is provided. The method may include receiving an inner pressure measurement of the flowing fluid from an inner pressure sensor disposed on an inner curvature portion of an arcuate tube section. In this regard, the arcuate tube section may be semi-circular. The method may further include receiving an outer pressure measurement of the flowing fluid from an outer pressure sensor disposed on an outer curvature portion of the arcuate tube section, determining, by processing circuitry, a pressure difference between the inner pressure measurement and the outer pressure measurement, and determining a mass flow rate of the flowing fluid passing through the arcuate tube section based on the pressure difference and a fluid density of the flowing fluid.

BRIEF DESCRIPTION OF THE SEVERAL VIEWS OF THE DRAWING(S)

Having thus described some non-limiting, example embodiments in general terms, reference will now be made to the accompanying drawings, which are not necessarily drawn to scale, and wherein:

DETAILED DESCRIPTION

Figure 1:
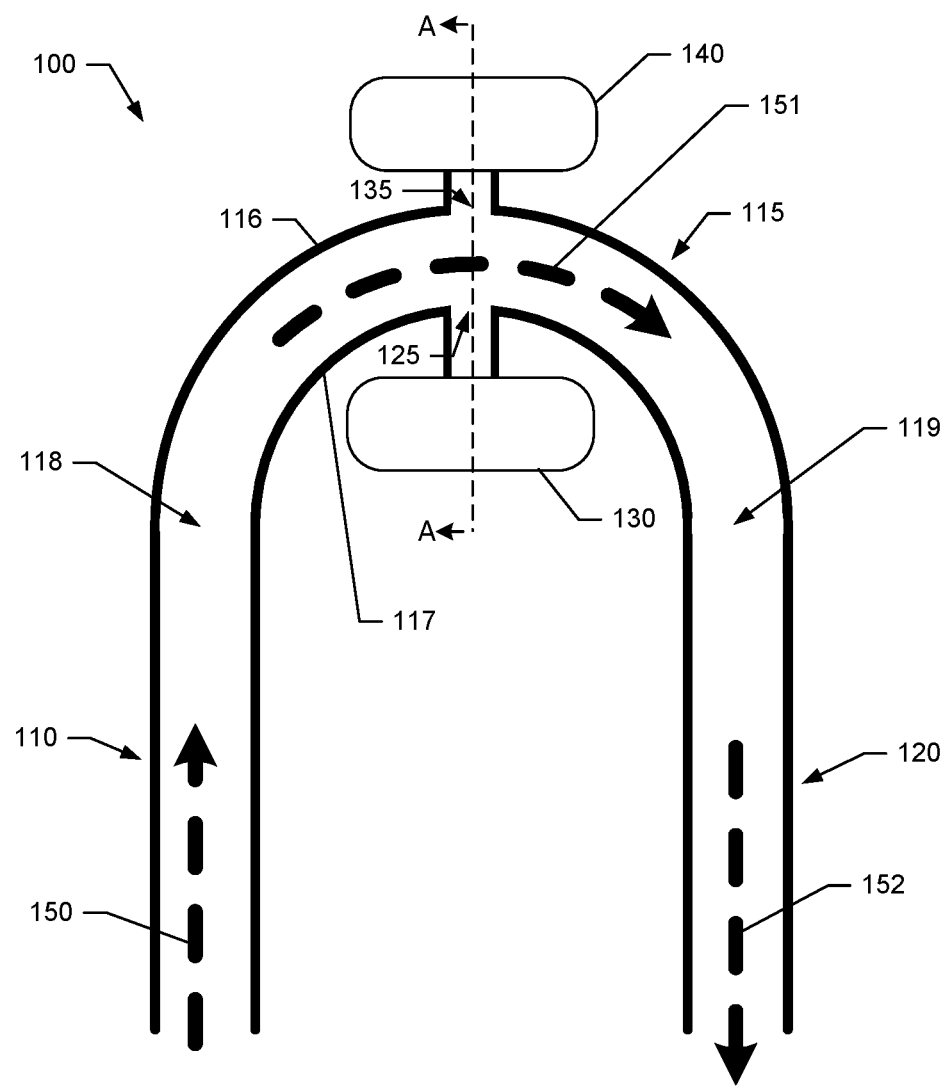
FIG. 1 illustrates an example mass flow meter according to some example embodiments.

Some non-limiting, example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true. As used herein, operable coupling should be understood to relate to direct or indirect connection that, in either case, enables functional interconnection of components that are operably coupled to each other.

In view of the forgoing, an example mass flow meter is provided that is, for example, capable of determining mass flow rates of a flowing fluid (e.g., liquid, gas, or combination thereof) even at low flow velocities or low system pressures. According to some example embodiments, the mass flow meter may pass the flowing fluid through an arcuate tube section having pressure sensors positioned to capture a differential pressure within the arcuate tube section. Based on structural characteristics of the arcuate tube section, the differential pressure can be used to determine a force caused by the flowing fluid on the interior of the arcuate tube section. Based on calculations associated with this force, along with other factors such as the absolute system pressure and the temperature of the flowing fluid, the mass flow rate can be determined accurately.

According to some example embodiments, the arcuate tube section may be semi-circular, and therefore centripetal force principles in a circular context can be leveraged. A measurement plane having a circular cross-section of the arcuate tube section may be defined at the apex of the arcuate tube section. An outer pressure sensor may be placed at the outer apex of the arcuate tube section (i.e., on the measurement plane) and an inner pressure sensor may be placed at an inner apex of the arcuate tube section (i.e., also at the measurement plane). The outer pressure sensor may capture an outer pressure measurement and the inner pressure sensor may capture an inner pressure measurement. The difference in the outer pressure measurement and the inner pressure measurement may be used to determine, for example, a force applied by the flowing fluid through the semi-circular arcuate tube section. As such, this force may be used with a centripetal force model to determine the mass flow rate of the flowing fluid through the arcuate tube section.

To determine the mass flow rate, the fluid density and the temperature may also need to be known or determined through measurement. In some relatively stable systems operating with a consistent fluid, the fluid density and the temperature may be stable and therefore known. However, if the fluid density and temperate vary, then measurements may be needed to determine the fluid density and the temperature at a given time. Such measurements may be captured coincident in time with the inner pressure measurement and the outer pressure measurement so that a complete representation of the system at a given time can be captured. Further, such measurements can be made continuously, possibly with time stamps, so that historical trends can be generated.

Having described some aspects in a general sense, reference is now made to FIG. 1, which illustrates an example mass flow meter 100. According to some example embodiments, the mass flow meter 100 includes an arcuate tube section 115. The arcuate tube section 115 may be curved or bent in accordance with desired parameters for operation of the mass flow meter 100. The bend in the arcuate tube section 115 can cause forces on the internal walls of the arcuate tube section 115 that may be indicated as a fluid pressure as fluid flows through the bend. By measuring the pressures within the bend, information about the flowing fluid can be gathered.

In the example embodiment of FIG. 1, the arcuate tube section 115 is formed with a semi-circular arc. In other words, a radius of curvature of the bend is constant throughout the 180-degree arc. The arcuate tube section 115 may include an outer apex that is positioned at a location having a farthest distance from both ends of the semi-circular arc formed by an outer curvature portion 116 of the arcuate tube section 115. The arcuate tube section 115 may also include an inner apex that is positioned at a location having a farthest distance from both ends of the semi-circular arc formed by an inner curvature portion 117 of the arcuate tube section 115. Accordingly, the outer apex and the inner apex may be aligned such that both the outer apex and the inner apex can reside in a plane defined by the outer apex, the inner apex, and a circular cross-section of the arcuate tube section 115 that includes the outer apex and the inner apex (i.e., the measurement plane).

According to some example embodiments, an outer apex opening 135 may be formed at the outer apex to provide access into the arcuate tube section 115 for an outer pressure sensor 140 to take measurements at that location. In this regard, the outer pressure sensor 140 may be configured measure the pressure of the fluid flowing through the arcuate tube section 115 at the outer apex. To optimize performance of the mass flow meter 100, the outer apex opening 135 may be formed in the arcuate tube section 115 to be a small as possible, while still permitting the pressure to be measured. As further described below, due to the semi-circular arc of the arcuate tube section 115, the pressure at the outer apex may be relatively high or a maximum pressure within the arcuate tube section 115. This is due to the angular momentum that is generated by the fluid flow, as indicated by arrow 151, through the semi-circular arc urging the fluid outward towards the outer apex. According to some example embodiments, the symmetric positioning of the outer pressure sensor 140 at the outer apex and the inner pressure sensor 130 at the inner apex of a semi-circular arc may operate to reduce or eliminate a number of variables in the mass flow meter 100 that would otherwise need to be accounted for in the determination of the mass flow rate.

According to some example embodiments, an inner apex opening 125 may be formed at the inner apex to provide access into the arcuate tube section 115 for an inner pressure sensor 140 to take measurements at that location. In this regard, the inner pressure sensor 130 may be configured to measure the pressure of the fluid flowing through the arcuate tube section 115 at the inner apex. To optimize performance of the mass flow meter 100, the inner apex opening 125 may be formed in the arcuate tube section 115 to be a small as possible, while still permitting the pressure to be measured. As further described below, due to the semi-circular arc of the arcuate tube section 115, the pressure at the inner apex may be relatively low or a minimum pressure within the arcuate tube section 115. This is due to the angular momentum that is generated by the fluid flow, as indicated by arrow 151, through the semi-circular arc urging the fluid outward towards the outer apex and away from the inner apex.

According to some example embodiments, the inner pressure sensor 130 and the outer pressure sensor 140 may be components of a differential pressure sensor. In this regard, according to some example embodiments, a component in the form of a differential pressure sensor may include two pressure transducers that may be configured to separately measure pressure at each location. However, according to some example embodiments, a differential pressure sensor may have a single transducer that is exposed or subjected to pressures at each of the sensor locations to provide a differential pressure measurement. In this regard, a sensor may be associated with each location where a pressure is being sensed, regardless of the number of transducers that may be included. As such, the differential pressure sensor may measure the pressure at each of the different locations (e.g., the inner apex and the outer apex) or the pressure may be collectively measured as a differential pressure between the different locations. Further, according to some example embodiments, the differential pressure sensor may include circuitry (e.g., which may be included in processing circuitry 510 described below) that determines a differential pressure between the two transducers.

According to some example embodiments, the outer pressure sensor 140 and the inner pressure sensor 130 may individually include a plurality of pressure sensors. In this regard, pressure sensors often have a range of pressures over which the sensor is usable. In some instances, the range may be rather limited. As such, according to some example embodiments, a plurality of pressure sensors may be used where each of the sensors within the plurality has a different range of operation. As a result, the mass flow meter 100 may be more flexible in application because a wider range of pressures may be measured by the outer pressure sensor 140 and the inner pressure sensor 130. Without multiple parallel sensors and using just a single sensor for each, a turndown ratio (i.e., the ratio of maximum readable flow to minimum readable flow) for the mass flow meter 100 may be realized as five to one. Obviously, improved turndown ratios may be realized by expanding the range of pressures that can be measured by introducing parallel sensors.

The pressure measurements at the outer apex and the inner apex can be used to determine a centripetal force generated by the flowing fluid within the arcuate tube section 115, as the fluid navigates through the turn or bend in the arcuate tube section 115. The centripetal force principles can be considered to determine this force, which may ultimately be useful in determining the mass flow rate of the fluid through the arcuate tube section 115.

The centripetal force in a semi-circular constraint may be expressed as $$F_{centripetal} = \frac{1}{2} m \frac{v^2}{r}$$

where m is mass, v is velocity, and r is the radius of the semi-circle. Additionally, m=ρV, where m is again the mass, ρ is the fluid density, and V is the volume may be considered. This same relationship can be leveraged for flows such that the mass flow rate equals the fluid density times the volumetric flow rate. Continuing along this line, the volumetric flow rate can be expressed in association with a cross-sectional area ($A_{cross-section}$) times the average velocity. Via substitution of these relationships, it can be determined that $$\Delta P = \frac{\rho d}{2r} \frac{\dot{Q}^2}{A_{cross-section}^2}$$

where r is the bend radius of the arcuate tube, d is the distance between the outer apex and inner apex, and $\dot{Q}$ is the volumetric flow rate. In other words, the centripetal force divided by the infinitesimal normal area of the outer apex of the arcuate tube section 115 is proportional to the pressure difference (e.g., the difference between the outer apex pressure and the inner apex pressure). Using these relationships, the pressure difference can be utilized to determine the mass flow rate through the arcuate tube section 115.

Referring again to the mass flow meter 100 of FIG. 1, linear tubing may be coupled to the ends of the arcuate tube section 115. The arcuate tube section 115 may have an arc tube input 118 and an arc tube output 119. According to some example embodiments, an input tube 110 may be coupled to the arc tube input 118 and an output tube 120 may be connected to the arc tube output 119. The input tube 110 and the output tube 120 may be linear extensions to the arc tube input 118 and the arc tube output 119, respectively. The function of the input tube 110 and the output tube 120 can be to ensure that fully developed fluid flow is passing into the arcuate tube section 115 and out of the mass flow meter 100. In this regard, a length of linear tubing can operate to calm chaotic behavior in the fluid flow as the fluid passes into the arcuate tube section 115. According to some example embodiments, the length of the input tube 110 and the length of the output tube 120 may be selected to ensure that fully developed fluid flow is realized independent of the direction of the fluid flow. In this regard, the lengths of the input tube 110 and the output tube 120 may be selected based on an inner diameter of the input tube 110 or the inner diameter of the output tube 120, as further described below.

Accordingly, a fluid may enter the mass flow meter 100 at the input tube 110, as indicated by the arrow 150. Within the input tube 110, a fully developed fluid flow may be achieved due to the length of the input tube 110. The fluid may then flow into the arcuate tube section 115 via the arc tube input 118. As indicated by the curvature of the arrow 151, the fluid may develop an angular momentum within the arcuate tube section 115 creating a relative high pressure at the outer apex opening 135 and a relative low pressure at the inner apex opening 125. The outer pressure sensor 140 may capture a measurement of the fluid pressure at the outer apex opening 135 and the inner pressure sensor 130 may capture a measurement of the fluid pressure at the inner apex opening 125. These measurements may be provided to processing circuitry, as described below, for analysis to determine the mass flow rate. The fluid may continue to flow out of the arcuate tube section 115 via the arc tube output 119, and into the output tube 120. Within the output tube 120, the fluid may flow out of the mass flow meter 100 as indicated by the arrow 152 into, for example, another fluid operating system.

Figure 2:
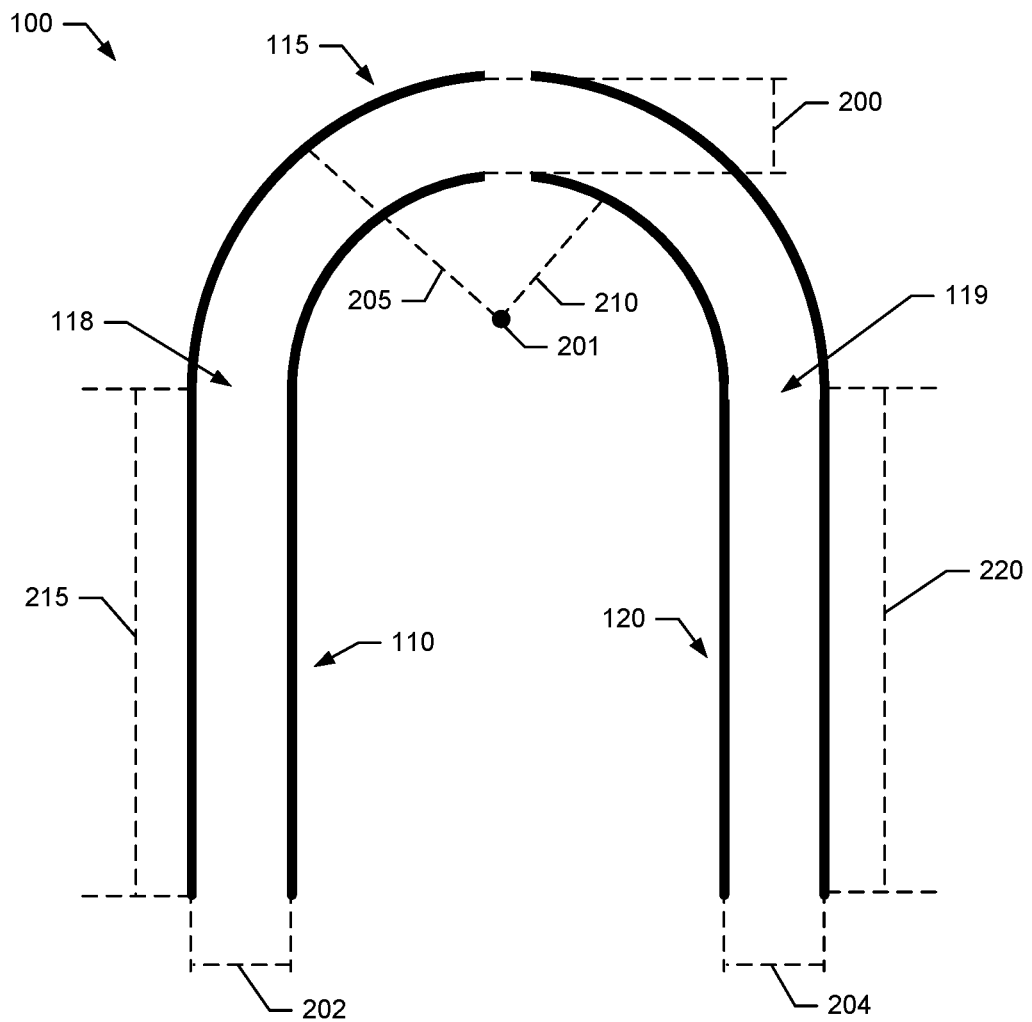
FIG. 2 illustrates an example construction of the tubing of a mass flow meter according to some example embodiments.

Now referring to FIG. 2, an architecture of the tubing of the mass flow meter 100 is shown without the pressure sensors 130 and 140. In this regard, the input tube 110 may have a length 215 and, similarly, the output tube 120 may have a length 220. Additionally, the input tube 110 and the output tube 120 may have a circular cross-section. Further, the input tube 110 may have an inner diameter 202 and the output tube 120 may have an inner diameter 204. According to some example embodiments, the inner diameter 202 may be same as the inner diameter 204. According to some example embodiments, to ensure fully developed fluid flow through the input tube 110 and entering the arcuate tube section 115, the length 215 of the input tube 110 may be greater than ten times the inner diameter 202 of the input tube 110. Similarly, according to some example embodiments, to ensure fully developed fluid flow through the output tube 120 and exiting the mass flow meter 100, the length 220 of the output tube 120 may be greater than ten times the inner diameter 204 of the output tube 120.

Additionally, with respect to the arcuate tube section 115, which in this example embodiment is semi-circular, a center of curvature 201 may be defined. With respect to the center of curvature, an inner radius 210 of the arcuate tube section 115 (to the interior wall) may be defined and an outer radius 205 of the arcuate tube section 115 (to the interior wall) may be defined. Because the arcuate tube section 115 is semi-circular, the outer radius 205 and the inner radius 210 may be may be constant from the arc tube input 118 to the arc tube output 119. Additionally, the arcuate tube section 115 may have a circular cross-section. Further, according to some example embodiments, the inner diameter 200 of the arcuate tube section 115 may be same as the inner diameter 202 of the input tube 110 and the inner diameter 204 of the output tube 120.

Figure 3:
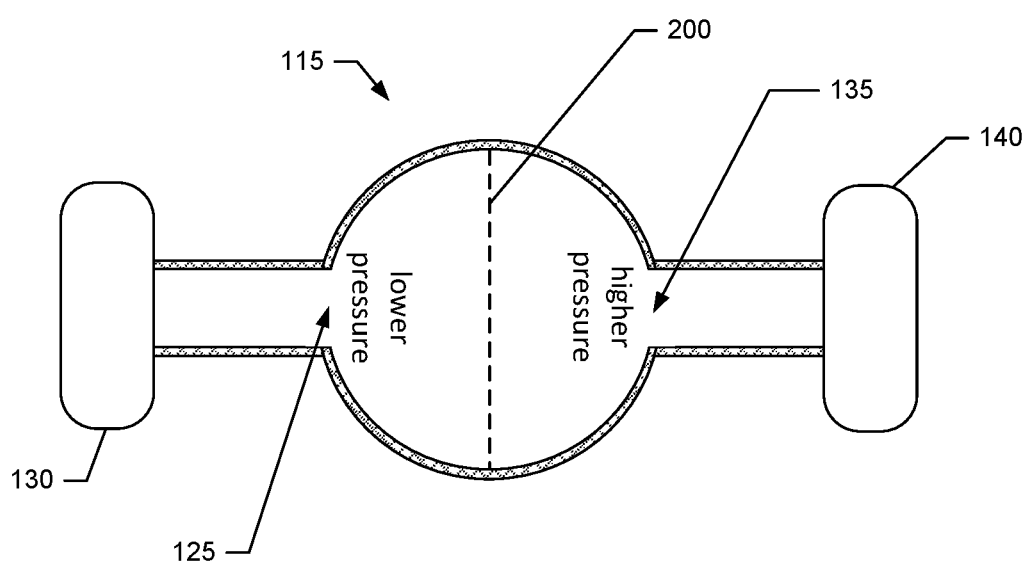
FIG. 3 illustrates a cross-section of the mass flow meter of FIG. 1 taken at A-A according to some example embodiments.

With reference to FIG. 3, a cross-section of the arcuate tube section 115 taken at A-A in FIG. 1 is shown. The cross-section is taken at the measurement plane, which may be defined as the plane that includes the outer apex, the inner apex, and is a circular cross-section of the arcuate tube section 115. As such, it can be seen that the outer pressure sensor 140 is coupled to the arcuate tube section 115 via the outer apex opening 135 to capture pressure measurements at the outer apex. Similarly, it can be seen that the inner pressure sensor 130 is coupled to the arcuate tube section 115 via the inner apex opening 125 to capture pressure measurements at the inner apex. As indicated in FIG. 3, a higher pressure is present at the outer apex opening 135 and a lower pressure is present at the inner apex opening 125, when a fluid is flowing through the arcuate tube section 115.

The mass flow meter 100 includes pressure sensors 130 and 140 to determine the differential pressure through the arcuate tube section 115. As described herein, this differential pressure (i.e., the difference between the pressure measurement of the inner pressure sensor 130 and the pressure measurement of the outer sensor 140) may be used to determine the volumetric flow rate given the fluid's density from which mass flow rate is also obtained. As mentioned above, in some systems, fluid density and temperature are constants (or substantially constant), and therefore these values may be known without the need for further sensors. However, in some instances, fluid density and temperature are variable, and therefore additional sensors may be employed to facilitate determining the fluid density, which is often dependent on temperature.

To determine temperature, a temperature sensor may be located within the mass flow meter (or elsewhere within a larger system), preferably, at a location that does not disturb the fluid flow within the mass flow meter. Additionally, to determine fluid density, the pressure of the system may be used. In this regard, the system pressure or absolute pressure of the system may be measured by an absolute pressure sensor that is located within the mass flow meter (or elsewhere within a larger system), preferably, at a location that does not disturb the fluid flow within the mass flow meter.

Figure 4:
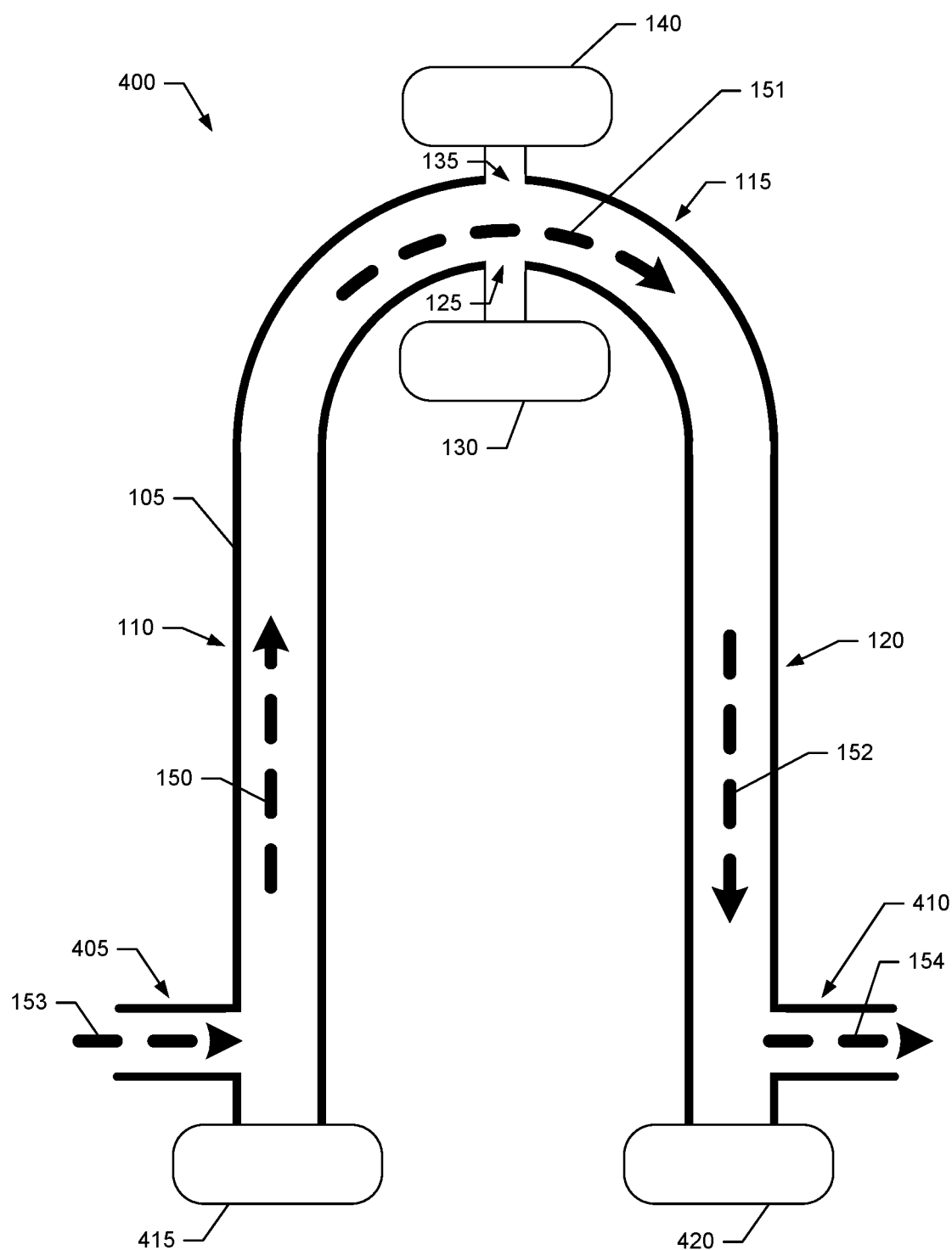
FIG. 4 illustrates another example mass flow meter according to some example embodiments.

In this regard, FIG. 4 illustrates a mass flow meter 400 that includes an absolute pressure sensor 415 and a temperature sensor 420. The mass flow meter 400 is a modified version of the mass flow meter 100 that operates in a similar manner. With respect to the differences, the fluid may flow into the mass flow meter 400 via a side input tube 405 that is coupled to the input tube 110 as indicated by arrow 153. Additionally, the fluid may flow out of the mass flow meter 400 via a side output tube 410 that is coupled to the output tube 120 as indicated by arrow 154.

Additionally, the input tube 110 may extend beyond the side input tube 405 to form a dead end at which an absolute pressure sensor 415 may be located. Because the absolute pressure sensor 415 may be located at the dead end where no flow occurs, the pressure measured by the absolute pressure sensor 415 may be unaffected by the fluid flow. As such, the measurements captured by the absolute pressure sensor 415 may be indicative of the standing pressure of the fluid within the system. Accordingly, the absolute pressure measurement captured by the absolute pressure sensor 415 may be used in determining the fluid density.

Additionally, the output tube 120 may extend beyond the side output tube 410 to form a dead end at which a temperature sensor 420 may be located. The temperature sensor 420 may take the form of any device capable of measuring a temperature within a desired range. For example, according to some example embodiments, the temperature sensor 420 may be thermocouple. Regardless of the type of temperature sensor 420, the temperature sensor 420 may positioned so as not to contribute to flow disturbance within the system and/or the mass flow meter 400. As such, the measurements captured by the temperature sensor 420 may be indicative of the temperature of the fluid within the system, and more specifically with the arcuate tube section 115. Accordingly, the temperature measurement captured by the temperature sensor 420 may be used in determining the fluid density.

According to some example embodiments, to determine fluid density within the tubing of the mass flow meter 400, a relationship involving the absolute pressure measurement and the temperature measurement may be used. In this regard, for example, a fluid density for a gas mixture at low pressures may be defined by taking mole fractions of the molecular weights of the component gases of the mixture and then multiplying by the absolute pressure measurement divided by the ideal gas constant times the absolute temperature measurement. As such, the fluid density may be determined in this manner using the measurements of the absolute pressure sensor 415 and the temperature sensor 420. Further, since the volumetric flow rate can be determined via the differential pressure from the pressure sensors 130 and 140, both the volumetric flow rate and the fluid density can be determined and used to determine the mass flow rate.

Figure 5:
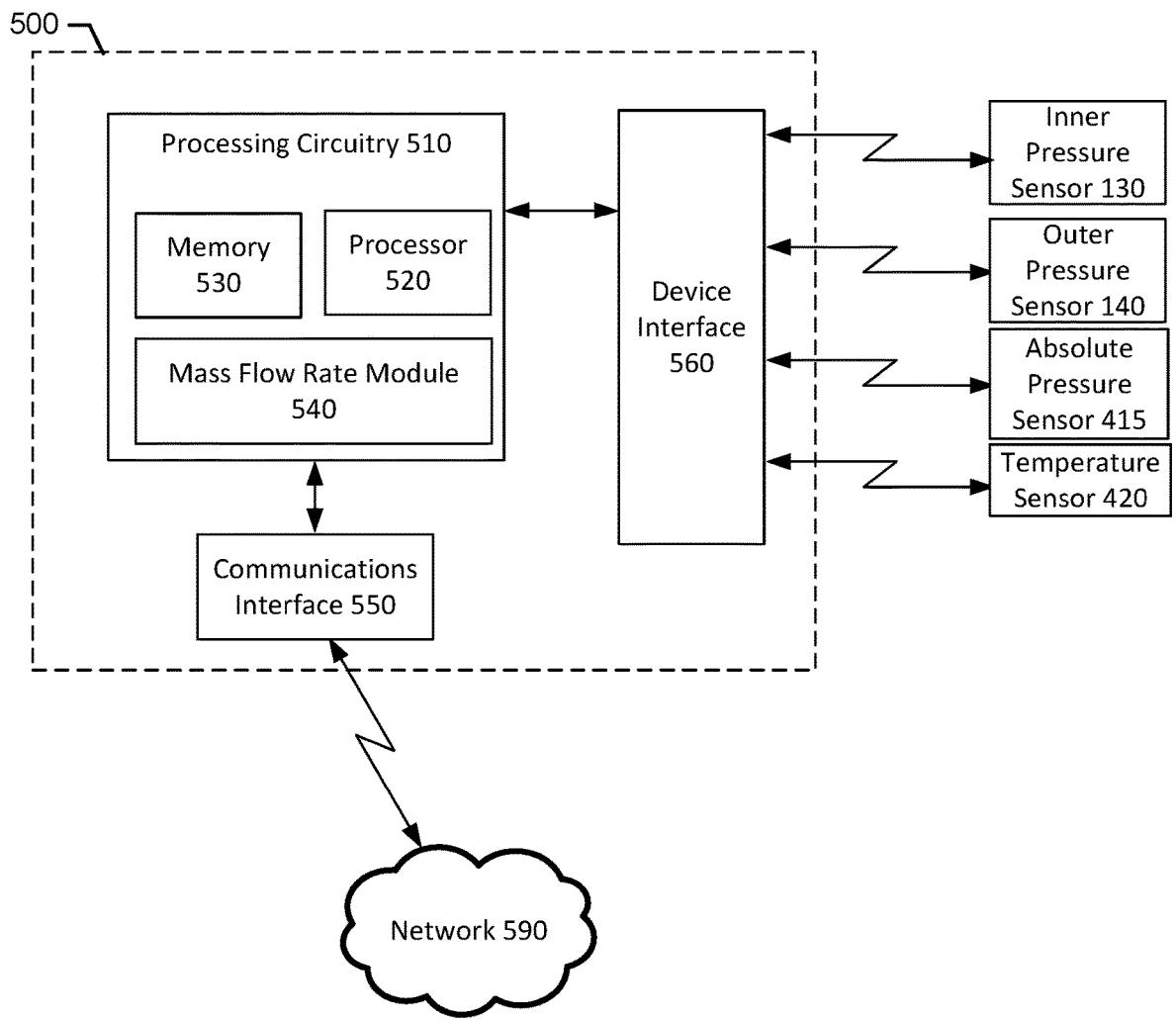
FIG. 5 illustrates an example block diagram of an apparatus configured to perform the processing of sensor measurements needed determine a mass flow rate according to some example embodiments.

Now referring to FIG. 5, according to some example embodiments, an example apparatus 500 is provided that may operate as a monitoring and analysis device of a mass flow meter. In this regard, the apparatus 500 may include circuitry that may be centralized in a single device or distributed across a number of devices. As such, according to some example embodiments, the functionalities described with respect to the apparatus 500 may be performed by a centralized device or some functionalities may be performed by circuitry of another device. The configuration of the apparatus 500 to perform the functionalities described herein may be performed by a number of distributed devices with circuitry to support to performance of the functionalities.

Therefore, according to some example embodiments, the apparatus 500 may include processing circuitry 510. Processing circuitry 510 may, in turn, include a processor 520, a memory 530, mass flow rate module 540, and a communications interface 550. Additionally, the apparatus 500 may include additional components not shown in FIG. 5 and the processing circuitry 510 may be operably coupled to other components of the apparatus 500 that are not shown in FIG. 5.

Further, according to some example embodiments, processing circuitry 510 may be in operative communication with or embody, the memory 530, the processor 520, mass flow rate module 540, and the communications interface 550. Through configuration and operation of the memory 530, the processor 520, the mass flow rate module 540, and the communications interface 550, the processing circuitry 510 may be configurable to perform various operations in association with tubing and sensors of a mass flow meter. In this regard, the processing circuitry 510 may be configured to perform computational processing, memory management, and, fluid flow control and monitoring, according to various example embodiments.

In some embodiments, the processing circuitry 510 may be embodied as a chip or chip set. In other words, the processing circuitry 510 may include one or more physical packages (e.g., chips) including materials, components or wires on a structural assembly (e.g., a baseboard). The processing circuitry 510 may be configured to receive inputs (e.g., via peripheral components, such as sensors), perform actions based on the inputs, and generate outputs (e.g., mass flow rate or the like). In an example embodiment, the processing circuitry 510 may include one or more instances of the processor 520, associated circuitry, and the memory 530. As such, the processing circuitry 510 may be embodied as a circuit chip (e.g., an integrated circuit chip, such as a field programmable gate array (FPGA)) configured (e.g., with hardware, software or a combination of hardware and software) to perform operations described herein.

In an example embodiment, the memory 530 may include one or more non-transitory memory devices such as, for example, volatile or non-volatile memory that may be either fixed or removable. The memory 530 may be configured to store information, data, applications, instructions, or the like for enabling, for example, the functionalities described with respect to the mass flow rate module 540. The memory 530 may operate to buffer instructions and data during operation of the processing circuitry 510 to support higher-level functionalities, and may also be configured to store instructions for execution by the processing circuitry 510. The memory 530 may also store various information including historical data. According to some example embodiments, various data stored in the memory 530 may be generated based on other received data (e.g., sensor measurements) and stored or the data may be retrieved via the communications interface 550 and stored in the memory 530.

As mentioned above, the processing circuitry 510 may be embodied in a number of different ways. For example, the processing circuitry 510 may be embodied as various processing means such as one or more processors 520 that may be in the form of a microprocessor, graphics processing unit, or other processing element, a coprocessor, a controller, or various other computing or processing devices including integrated circuits such as, for example, an ASIC (application specific integrated circuit), an FPGA, or the like. In an example embodiment, the processing circuitry 510 may be configured to execute instructions stored in the memory 530 or otherwise accessible to the processing circuitry 510. As such, whether configured by hardware or by a combination of hardware and software, the processing circuitry 510 may represent an entity (e.g., physically embodied in circuitry—in the form of processing circuitry 510) capable of performing operations according to example embodiments while configured accordingly. Thus, for example, when the processing circuitry 510 is embodied as an ASIC, FPGA, or the like, the processing circuitry 510 may be specifically configured hardware for conducting the operations described herein. Alternatively, as another example, when the processing circuitry 510 is embodied as an executor of software instructions, the instructions may specifically configure the processing circuitry 510 to perform the operations described herein.

The communications interface 550 may include one or more interface mechanisms for enabling communication with other devices external to the apparatus 500, via, for example, network 590, which may, for example, be a serial network, a local area network, the Internet, or the like, through a direct (wired or wireless) communication link to another external device, or the like. In some cases, the communications interface 550 may be any means such as a device or circuitry embodied in either hardware, or a combination of hardware and software that is configured to receive or transmit data from/to devices in communication with the processing circuitry 510. The communications interface 550 may be a wired or wireless interface and may support various communications protocols (WIFI®, BLUETOOTH®, cellular, RS-232, RS-485, or the like).

The device interface 560 may be input/output interface that operates between the processing circuitry 510 and peripheral devices that are controlled by and/or provide data to the processing circuitry 510. According to some example embodiments, the device interface 560 may be integrated into the processing circuitry 510 or the device interface 560 may be housed in a separate component configured to translate or otherwise interface with the peripheral devices in a manner that the processing circuitry 510 may not be able to directly. However, according to some example embodiments, the processing circuitry 510 may be configured to directly interface with peripheral devices.

In this regard, via the device interface 560, the processing circuitry 510 may be configured to interface with the inner pressure sensor 130, the outer pressure sensor 140, the absolute pressure sensor 415, and the temperature sensor 420. In this regard, processing circuitry 510 may be configured to interface with the sensors 130, 140, 415, and 420 to receive measurements captured by one or more of the sensors 130, 140, 415, and 420 for use in an analysis of the measurements. Additionally, the processing circuitry 510 may be configured to control the operation of the sensors 130, 140, 415, and 420, such as the sampling rate of the sensors or other operational settings or parameters. As mentioned above, each sensor 130, 140, 415, and 420 may include a number of parallel-operated sensors have different ranges for operation (e.g., different pressure ranges of operation). As such, the processing circuitry 510 may be configured to determine a current operating condition and monitor the parallel-operated sensor that is designed for operation in the range of the current operating condition for receiving measurements and other data.

The mass flow rate module 540 may, according to some example embodiments, be circuitry that is part of or a configuration of the processor 520, possibly in combination with the memory 530. As such, the mass flow rate module 540 may be configured to cause the processing circuitry 510 to perform various functionalities as a component of the processing circuitry 510. As such, the mass flow rate module 540, and thus the processing circuitry 510, may be configured to control and receive measurements from some or all of the sensors 130, 140, 415, and 420.

According to some example embodiments, the mass flow rate module 540 may be configured to receive an inner pressure measurement of a flowing fluid from the inner pressure sensor 130, which may be disposed on an inner curvature portion of an arcuate tube section of a mass flow meter. Additionally, the mass flow rate module 540 may be configured to receive an outer pressure measurement of the flowing fluid from the outer pressure sensor 140, which may be disposed on an outer curvature portion of the arcuate tube section of the mass flow meter.

In some example embodiments, the fluid density and the fluid temperature may be known (e.g., substantially stable) and the values may be stored, for example, in the memory 530 for use in determinations of, for example, the mass flow rate. However, in example embodiments where the fluid density and the temperature fluctuate, the absolute pressure sensor 415 and the temperature sensor 420 may be implemented to capture measurements for these fluid characteristics or that can be used to determine these fluid characteristics. As such, according to some example embodiments, a mass flow meter may include the absolute pressure sensor 415 and the temperature sensor 420 and the mass flow rate module 540 may be configured to receive measurements from the absolute pressure sensor 415 and the temperature sensor 420. In this regard, the mass flow rate module 540 may be configured to receive an absolute pressure measurement within tubing of the mass flow meter from the absolute pressure sensor 415. Further, the mass flow rate module 540 may be configured to receive a temperature measurement within the tubing of the mass flow meter from temperature sensor.

Based on the measurements received by the mass flow rate module 540, the mass flow rate module 540 may be configured to determine various fluid characteristics and fluid flow characteristics with the mass flow meter. In this regard, according to some example embodiments, a volumetric flow may be determined based on the inner pressure measurement, the outer pressure measurement, and the fluid's density. According to some example embodiments, the cross-sectional area of the arcuate tube section and bend radius of the arcuate tube section at the measurement plane may be known (e.g., stored in the memory 530), the fluid density may be known or determined, and these values may be used to determine volumetric flow. This information might also be determined in the form of a calibration coefficient and stored in memory for more efficient computation.

Further, according to some example embodiments, a mass flow rate may be determined. To determine the mass flow rate, the inner pressure measurement and the outer pressure measurement may be used to determine a pressure difference at the measurement plane. Using the pressure difference, with the fluid density, which often depends on the temperature, the mass flow rate may be determined. If the fluid density is not known, the absolute pressure measurement, the temperature measurement, and the fluid's composition may be used to determine the fluid's density. The temperature may be taken directly from the temperature sensor 420.

The mass flow rate module 540 may therefore be configured with the model of the mass flow meter tubing. The model may be mathematical model that is based on the structure of the tubing of the mass flow meter. For example, the mathematical model may be based circular centripetal force principles when the arcuate tube section of the mass flow meter is semi-circular. As such, based on this and other architectural characteristics of the tubing (e.g., the inner radius of the tubing at the measurement plane), the mathematical model may be determined and stored for use in determining, for example, mass flow rate and other characteristics of the fluid flowing through the arcuate tube section.

Figure 6:
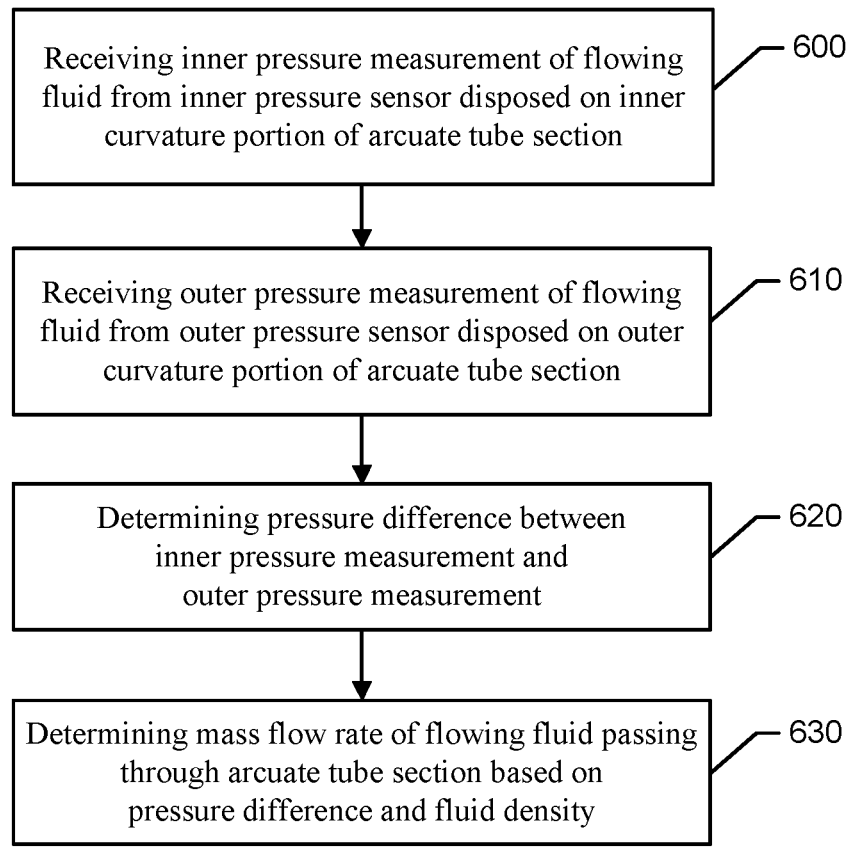
FIG. 6 illustrates flowchart of an example method for determining a flow rate according to some example embodiments.

Now referring to FIG. 6, an example method for determining, by a mass flow meter, a mass flow rate of a flowing fluid is provided, as shown in the flowchart of FIG. 6. In this regard, the example method may include, at 600, receiving an inner pressure measurement of the flowing fluid from an inner pressure sensor disposed on an inner curvature portion of an arcuate tube section. At 610, the example method may include receiving an outer pressure measurement of the flowing fluid from an outer pressure sensor disposed on an outer curvature portion of the arcuate tube section. Further, at 620, the example method may include determining, by processing circuitry, a pressure difference between the inner pressure measurement and the outer pressure measurement. The example method may further include, at 630, determining a mass flow rate of the flowing fluid passing through the arcuate tube section based on the pressure difference and a fluid density.

According to some example embodiments, the arcuate tube section may be a semi-circular tube section. Also, the flowing fluid may cause a centripetal force on an interior surface of the arcuate tube section. Additionally or alternatively, the method may further include capturing, by the outer pressure sensor, the outer pressure measurement at an outer apex of the semi-circular tube section, and capturing, by the inner pressure sensor, the inner pressure measurement at an inner apex of the semi-circular tube section. Additionally or alternatively, a linear input tube section may be coupled to an arc tube input of the arcuate tube section. Further, in this regard, according to some example embodiments, a length of the linear input tube section may be at least ten times an inner diameter of the arcuate tube section. Additionally or alternatively, a linear output tube section may be coupled to an arc tube output of the arcuate tube section. The linear output tube section being at least as long as the linear input tube section.

According to some example embodiments, the example method may further include receiving an absolute pressure measurement within tubing of the mass flow meter from an absolute pressure sensor, and receiving a temperature measurement within the tubing of the mass flow meter from temperature sensor. In this regard, the example method may further include determining a fluid density of the flowing fluid based on the absolute pressure measurement and the temperature measurement. Additionally, according to some example embodiments, determining the mass flow rate may include determining the mass flow rate based on the pressure difference and the fluid density.

As used herein, the term "module" is intended to include a computer-related entity, such as but not limited to hardware, software, or a combination of hardware and software. For example, a module may be, but is not limited to being a software or hardware implementation of a process, an object, an executable, and/or a thread of execution, which may be implemented via a processor or computer. By way of example, both an application running on a computing device and/or the computing device can be a module. One or more modules can reside within a process and/or thread of execution and a module may be localized on one computer and/or distributed between two or more computers. In addition, these modules can execute from various computer readable media having various data structures stored thereon. The modules may communicate by way of local and/or remote processes such as in accordance with a signal having one or more data packets, such as data from one module interacting with another module in a local system, distributed system, and/or across a network such as the Internet with other systems by way of the signal. Each respective module may perform one or more functions that will be described in greater detail herein. However, it should be appreciated that although such examples are described in terms of separate modules corresponding to various functions performed, some examples need not necessarily utilize modular architectures for employment of the respective different functions. Thus, for example, code may be shared between different modules, or the processing circuitry itself may be configured to perform all of the functions described as being associated with the modules described herein. Furthermore, in the context of this disclosure, the term "module" should not be understood as a nonce word to identify any generic means for performing functionalities of the respective modules. Instead, the term "module" should be understood to be a modular entity that is specifically configured in, or can be operably coupled to, processing circuitry to modify the behavior and/or capability of the processing circuitry based on the hardware and/or software that is added to or otherwise operably coupled to the processing circuitry to configure the processing circuitry accordingly.

Many modifications and other embodiments of the measuring device set forth herein will come to mind to one skilled in the art to which these inventions pertain having the benefit of the teachings presented in the foregoing descriptions and the associated drawings. Therefore, it is to be understood that the measuring devices are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits, or solutions described herein should not be thought of as being critical, required, or essential to all embodiments or to that which is claimed herein. Although specific terms are employed herein, they are used in a generic and descriptive sense only and not for purposes of limitation.

What is claimed is:

1. A mass flow meter comprising:
   an arcuate tube section having an arc tube input for receiving a flowing fluid into the arcuate tube section and an arc tube output for outputting the flowing fluid out of the arcuate tube section, the arcuate tube section comprising a semi-circular tube section;
   an inner pressure sensor disposed on an inner curvature portion of the arcuate tube section and configured to capture an inner pressure measurement of the flowing fluid;
   an outer pressure sensor disposed on an outer curvature portion of the arcuate tube section and configured to capture an outer pressure measurement of the flowing fluid; and
   processing circuitry configured to:
      receive the inner pressure measurement from the inner pressure sensor;
      receive the outer pressure measurement from the outer pressure sensor;
      determine a pressure difference between the inner pressure measurement and the outer pressure measurement; and
      determine a mass flow rate of the flowing fluid passing through the arcuate tube section based on the pressure difference and a fluid density of the flowing fluid.

2. The mass flow meter of claim 1, wherein the flowing fluid causes a centripetal force on an interior surface of the arcuate tube section.

3. The mass flow meter of claim 2, wherein the semi-circular tube section comprises an outer apex and an inner apex;
   wherein the outer pressure sensor is operably coupled at the outer apex to capture the outer pressure measurement at the outer apex; and
   wherein the inner pressure sensor is operably coupled at the inner apex to capture the inner pressure measurement at the inner apex.

4. The mass flow meter of claim 1, further comprising a linear input tube section coupled to the arc tube input.

5. The mass flow meter of claim 4, wherein a length of the linear input tube section is at least ten times an inner diameter of the arcuate tube section.

6. The mass flow meter of claim 4, further comprising a linear output tube section coupled to the arc tube output, the linear output tube section being at least as long as the linear input tube section to permit the mass flow meter to operate with flowing fluid moving in either direction through the arcuate tube section.

7. The mass flow meter of claim 1, wherein the inner pressure sensor is disposed on an opposite side of the arcuate tube section from the outer pressure sensor.

8. The mass flow meter of claim 1, further comprising:
an absolute pressure sensor configured to capture an absolute pressure measurement within tubing of the mass flow meter; and
a temperature sensor configured to capture a temperature measurement of the flowing fluid within the tubing of the mass flow meter.

9. The mass flow meter of claim 8, wherein the processing circuitry is further configured to:
receive the absolute pressure measurement;
receive the temperature measurement; and
determine the fluid density of the flowing fluid based on the absolute pressure measurement and the temperature measurement;
wherein the processing circuitry is further configured to determine the mass flow rate based on the fluid density.

10. A mass flow meter comprising:
an arcuate tube section having an arc tube input for receiving a flowing fluid into the arcuate tube section and an arc tube output for outputting the flowing fluid out of the arcuate tube section, the arcuate tube section being formed in a semi-circular arc;
an inner pressure sensor disposed at an inner apex of the arcuate tube section and configured to capture an inner pressure measurement of the flowing fluid at the inner apex;
an outer pressure sensor disposed at an outer apex of the arcuate tube section and configured to capture an outer pressure measurement of the flowing fluid at the outer apex;
an absolute pressure sensor configured to capture an absolute pressure measurement within tubing of the mass flow meter;
a temperature sensor configured to capture a temperature measurement of the flowing fluid within the tubing of the mass flow meter; and
processing circuitry configured to:
receive the inner pressure measurement, the outer pressure measurement, the absolute pressure measurement, and the temperature measurement;
determine a pressure difference between the inner pressure measurement and the outer pressure measurement;
determine a fluid density of the flowing fluid based on the absolute pressure measurement and the temperature measurement; and
determine a mass flow rate of the flowing fluid passing through the arcuate tube section based on the pressure difference and the fluid density.

11. The mass flow meter of claim 10, further comprising a linear input tube section coupled to the arc tube input.

12. The mass flow meter of claim 11, wherein a length of the linear input tube section is at least ten times an inner diameter of the arcuate tube section.

13. The mass flow meter of claim 12, further comprising a linear output tube section coupled to the arc tube output, the linear output tube section being at least as long as the linear input tube section.

14. A method for determining, by a mass flow meter, a mass flow rate of a flowing fluid, the method comprising:
receiving an inner pressure measurement of the flowing fluid from an inner pressure sensor disposed on an inner curvature portion of an arcuate tube section, the arcuate tube section including a semi-circular tube section;
receiving an outer pressure measurement of the flowing fluid from an outer pressure sensor disposed on an outer curvature portion of the arcuate tube section;
determining, by processing circuitry, a pressure difference between the inner pressure measurement and the outer pressure measurement; and
determining the mass flow rate of the flowing fluid passing through the arcuate tube section based on the pressure difference and a fluid density of the flowing fluid.

15. The method of claim 14, wherein the flowing fluid causes a centripetal force on an interior surface of the arcuate tube section.

16. The method of claim 15, wherein the method further comprises:
capturing, by the outer pressure sensor, the outer pressure measurement at an outer apex of the semi-circular tube section; and
capturing, by the inner pressure sensor, the inner pressure measurement at an inner apex of the semi-circular tube section.

17. The method of claim 14, wherein a linear input tube section is coupled to an arc tube input of the arcuate tube section.

18. The method of claim 17, wherein a length of the linear input tube section is at least ten times an inner diameter of the arcuate tube section.

19. The method of claim 17, wherein a linear output tube section is coupled to an arc tube output of the arcuate tube section, the linear output tube section being at least as long as the linear input tube section.

20. The method of claim 14, further comprising:
receiving an absolute pressure measurement within tubing of the mass flow meter from an absolute pressure sensor;
receiving a temperature measurement within the tubing of the mass flow meter from temperature sensor; and
determining the fluid density of the flowing fluid based on the absolute pressure measurement and the temperature measurement;
wherein determining the mass flow rate comprises determining the mass flow rate based on the pressure difference and the fluid density.

\* \* \* \* \*